US009903854B2

(12) United States Patent
Lee et al.

(10) Patent No.: US 9,903,854 B2
(45) Date of Patent: Feb. 27, 2018

(54) SELF-POWERED BLOOD COAGULATION CHIP FOR INR VALUE AND HEMATOCRIT DETERMINATION

(71) Applicant: THE REGENTS OF THE UNIVERSITY OF CALIFORNIA, Oakland, CA (US)

(72) Inventors: Luke P. Lee, Orinda, CA (US); John R. Waldeisen, Berkeley, CA (US); Ivan Dimov, Palo Alto, CA (US); Benjamin M. Ross, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 83 days.

(21) Appl. No.: 14/632,021

(22) Filed: Feb. 26, 2015

(65) Prior Publication Data

US 2015/0233894 A1  Aug. 20, 2015

Related U.S. Application Data

(63) Continuation of application No. PCT/US2013/057663, filed on Aug. 30, 2013.
(Continued)

(51) Int. Cl.
*G01N 33/00* (2006.01)
*G01N 33/49* (2006.01)
*G01N 33/86* (2006.01)

(52) U.S. Cl.
CPC ....... *G01N 33/4905* (2013.01); *G01N 33/491* (2013.01); *G01N 33/86* (2013.01)

(58) Field of Classification Search
None
See application file for complete search history.

(56) References Cited

U.S. PATENT DOCUMENTS 4,906,439 A * 3/1990 Grenner ............ B01L 3/502707
422/417
4,959,324 A * 9/1990 Ramel .................. B01L 3/5023
422/408

(Continued)

OTHER PUBLICATIONS

Korean Intellectual Property Office (KIPO), International Search Report and Written Opinion, related PCT International Application No. PCT/US2013/057663, dated Nov. 27, 2013, pp. 1-11, with claims examined, pp. 12-20.

*Primary Examiner* — Jill Warden
*Assistant Examiner* — Brittany Fisher
(74) *Attorney, Agent, or Firm* — O'Banion & Ritchey LLP; John P. O'Banion

(57) ABSTRACT

A point-of-test diagnostic chip that is capable of simultaneous evaluation of blood coagulation time (INR Value) and hematocrit level. A finger prick volume of blood is placed at the inlet of the device, and the residual vacuum contained within the device provides a pressure gradient to drive the flow of whole blood. The INR value is determined by the distance the blood traverses down the channel before it coagulates. The channel is primed with tissue factor and phospholipids to induce coagulation. A control channel is primed with anticoagulants for use as a way to normalize initial loading times. The hematocrit level is determined by sedimentation of blood cells into a trench and the interface between blood cells that have overfilled the trench and plasma provide a visual readout.

24 Claims, 4 Drawing Sheets

Related U.S. Application Data

(60) Provisional application No. 61/695,932, filed on Aug. 31, 2012.

(56) References Cited

U.S. PATENT DOCUMENTS

| | | | | |
|---|---|---|---|---|
| 5,132,086 A | * | 7/1992 | Allen | C12Q 1/60 |
| | | | | 422/408 |
| 5,260,221 A | * | 11/1993 | Ramel | B01L 3/5023 |
| | | | | 422/408 |
| 6,200,532 B1 | | 3/2001 | Wu et al. | |
| 6,607,644 B1 | * | 8/2003 | Apffel, Jr. | G01N 33/521 |
| | | | | 204/450 |
| 2004/0019300 A1 | * | 1/2004 | Leonard | G01N 33/491 |
| | | | | 600/584 |
| 2004/0191124 A1 | * | 9/2004 | Noetzel | B01L 3/502746 |
| | | | | 422/69 |
| 2007/0062822 A1 | | 3/2007 | Fujiwara et al. | |
| 2007/0134810 A1 | * | 6/2007 | Yang | G01N 33/54366 |
| | | | | 436/514 |
| 2009/0107909 A1 | * | 4/2009 | Kotera | B01L 3/502753 |
| | | | | 210/513 |
| 2009/0177117 A1 | | 7/2009 | Amano et al. | |
| 2009/0240123 A1 | | 9/2009 | Siebrecht et al. | |
| 2012/0177537 A1 | * | 7/2012 | Aota | G01N 1/4005 |
| | | | | 422/69 |

* cited by examiner

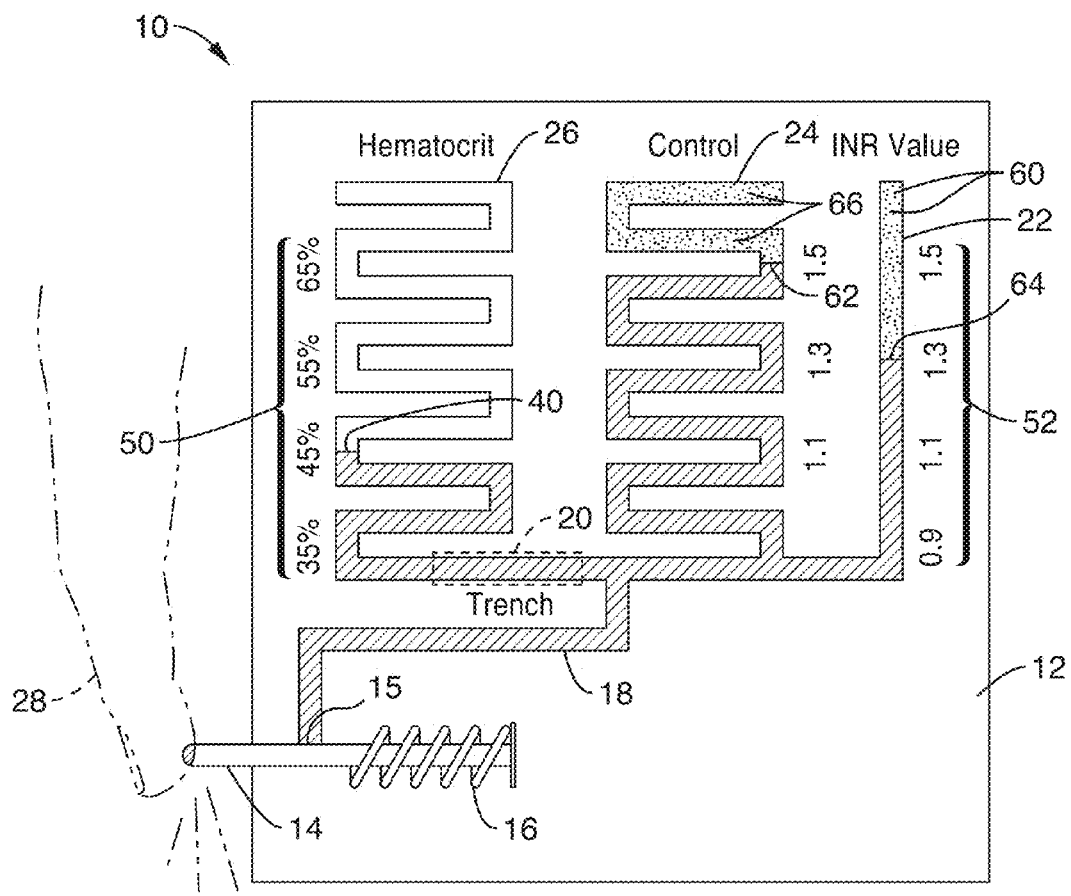
FIG. 1
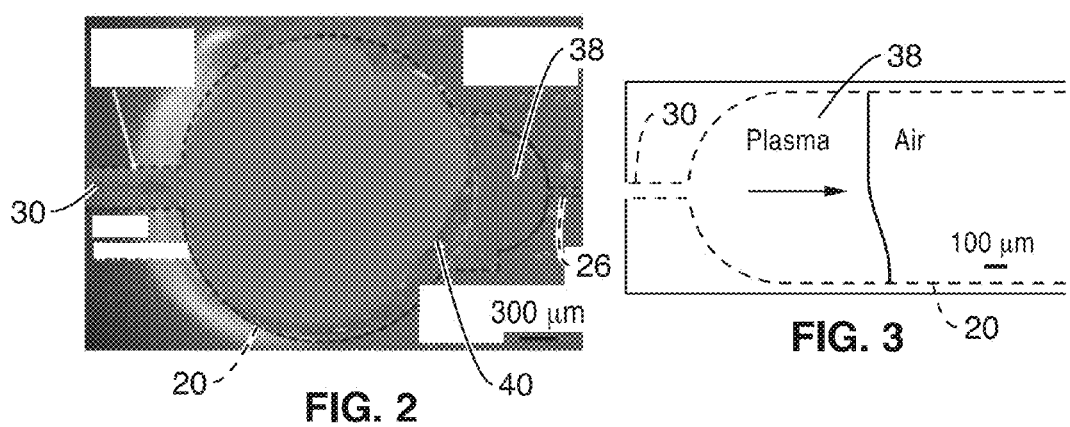
FIG. 2   FIG. 3

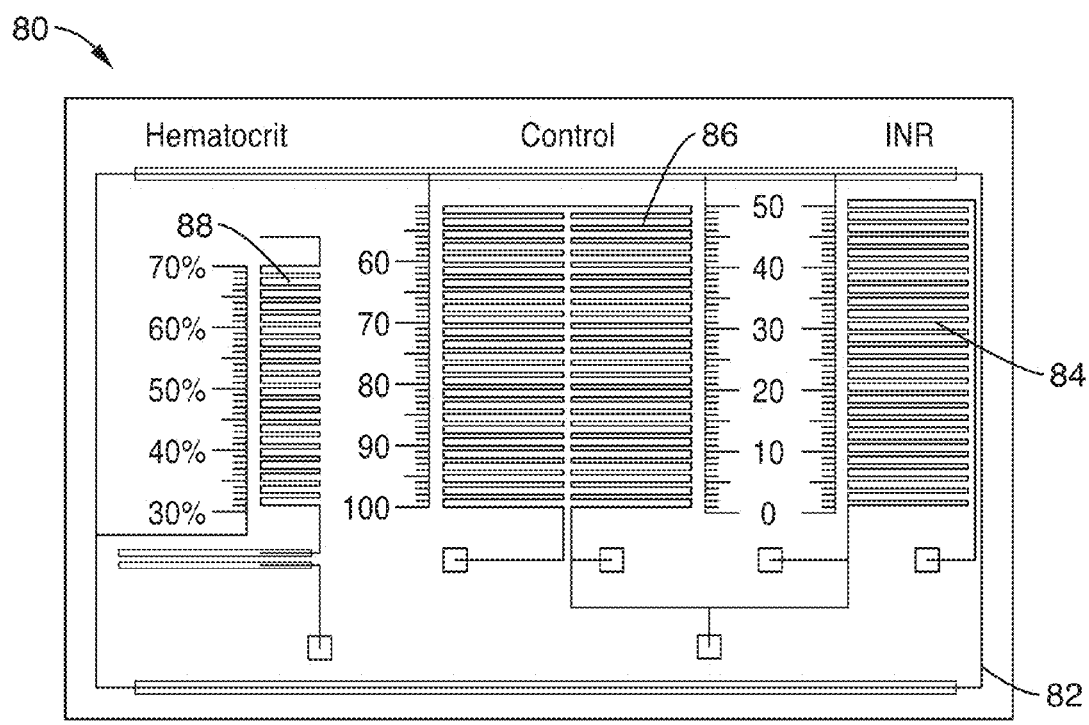
FIG. 5
FIG. 6
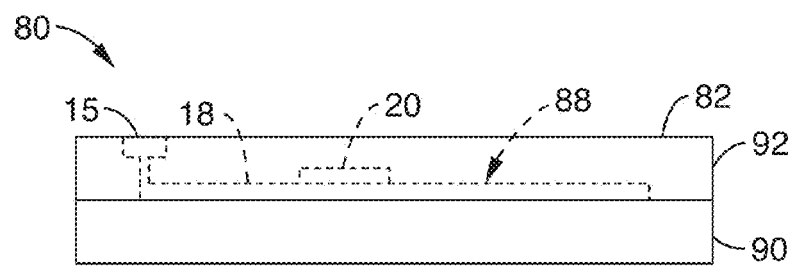
FIG. 7

US 9,903,854 B2

SELF-POWERED BLOOD COAGULATION CHIP FOR INR VALUE AND HEMATOCRIT DETERMINATION

CROSS-REFERENCE TO RELATED APPLICATIONS

This application is a 35 U.S.C. § 111(a) continuation of PCT international application number PCT/US2013/057663 filed on Aug. 30, 2013, incorporated herein by reference in its entirety, which claims priority to, and the benefit of, U.S. provisional patent application Ser. No. 61/695,932 filed on Aug. 31, 2012, incorporated herein by reference in its entirety. Priority is claimed to each of the foregoing applications.

The above-referenced PCT international application was published as PCT International Publication No. WO 2014/036484 on Mar. 6, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to blood sensing, and more particularly to blood coagulation time and hematocrit level sensing.

2. Description of Related Art

The administration of anticoagulants has become a routine healthcare tool to prevent and combat a number of patient health problems. The prescription of oral anticoagulants (e.g. coumarins, direct thrombin inhibitors, etc.) is typically used as a long-term prophylaxis to prevent thrombosis in a number of "chronic" situations. For example, this includes patients with long-term health concerns such as atrial fibrillation, past episodes of embolism or stroke, inherited/acquired thrombophilic disorders, and surgeries such as those involving prosthetic heart valve replacement, coronary artery stent implantation, or orthopedic surgery (e.g. knee or hip replacements).

As a result of the widespread use of anticoagulants, 2.5 million Americans now rely on blood thinners annually. However, the most commonly used oral anticoagulants, coumarins, have a number of adverse side effects that require continual blood monitoring and alteration of the drug dosage administered to the patient. The activity of coumarins, which are vitamin K antagonists, responds to a number of factors such as diet (foods high in vitamin K, cranberries, green vegetables), liver, kidney, and thyroid dysfunction, alcohol, several herbs and spices, and many commonly used drugs such as aspirin and certain antibiotics. Consequently, in 2005 the International Self-Monitoring Association for Oral Anticoagulation reviewed and advocates for the increased practice of patient self-testing as a means to counter the variability in initial dose selection and stabilization, as well as long-term difficulties in maintaining anticoagulant stability. Among the benefits of self-monitoring were improved quality of life, greater cost-effectiveness, patient education, and a decreased risk of death from hemorrhage.

Unfortunately, the self-management of coagulation has not become a commonplace phenomenon as it has been with the use of glucose monitors to manage diabetes. A number of self-monitors are available on the market, such as the Roche CoaguChek and the HemoSense INRatio, yet these devices cost between $500-$2,000. In contrast, glucose monitors cost two orders of magnitude less and can generally be purchased for less than $20. A number of variables are at fault for this price differential. One aspect is that some coagulation monitors rely on more expensive technology like the CoaguChek, which detects the proteolytic cleavage of a fluorescent peptide. However, other monitors such as the INRatio, which electrochemically measures a change in impedance due to clot formation, are much cheaper and similar technologies to a glucose monitor, but still cost ~$500.

It is suspected that slow user adoption has not created a sustainable market that can survive upon small profit margins, thus the exorbitantly inflated price of blood monitors. To compound this issue, patient self-testing occurs on a monthly to weekly basis. This is a stark contrast to diabetics who test on a daily basis, perhaps as many as 3-10 times per day, thus using more consumables. In order for the self-monitoring of blood coagulation to become widespread, a cheap and more basic product that emulates a pregnancy lateral flow assay may drastically improve adoption. Even though pregnancy tests are used infrequently, their simplicity and robustness enable widespread accessibility.

Accordingly, an object of the present invention is a blood coagulation chip with attributes that are more similar to a lateral flow assay than to a glucose monitor.

BRIEF SUMMARY OF THE INVENTION

One aspect of the present invention is a point-of-test diagnostic chip to simultaneously determine blood coagulation time (INR Value) and hematocrit level. The chip is configured to be a simple, disposable device that can be cheaply mass fabricated using hot embossing or injection molding techniques.

In one embodiment, a finger prick volume of blood is placed at the inlet of the device, and the residual vacuum contained within the device provides a pressure gradient to drive the flow of whole blood. The INR value is determined by the distance the blood traverses down the channel before it coagulates. The channel is primed with tissue factor and phospholipids to induce coagulation. A control channel is primed with anticoagulants for use as a way to normalize initial loading times. The hematocrit level is determined by sedimentation of blood cells into a trench and the interface between blood cells that have overfilled the trench and plasma provide a visual readout.

Another aspect of the invention is to provide a self-management tool for people with chronic bleeding disorders or those who use oral anticoagulants as a long-term prophylaxis. The device may also be beneficial to physicians in the developing world and resource-limited areas.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a schematic diagram of a self-loading, polymeric blood coagulation chip configured to simultaneously measure hematocrit and prothrombin time (INR value).

FIG. 2 is an image demonstrating a top view of the self-powered plasma skimming trench in accordance of the present invention.

FIG. 3 is a schematic diagram of the trench of FIG. 2.

FIG. 5 is a schematic view of the back side of the polymeric blood coagulation chip of FIG. 1.

FIG. 6 is a top view schematic diagram of an exemplary self-loading, polymeric blood coagulation chip comprising a two-layer device with one of the layers comprising trenches for blood cell sedimentation and large vacuum reservoirs.

FIG. 7 is a side view schematic diagram of the self-loading, polymeric blood coagulation chip of FIG. 6.

DETAILED DESCRIPTION OF THE INVENTION

Figure 4A:
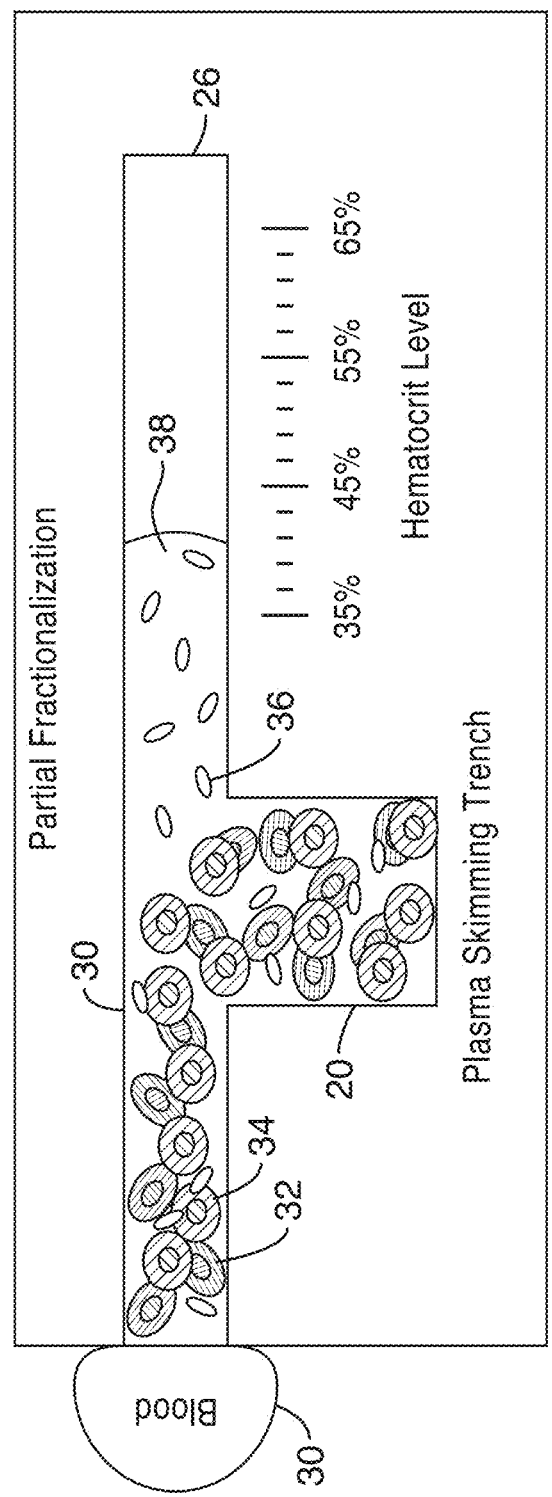
FIG. 4A is a schematic diagram of the interface between transparent plasma and blood as a result of the plasma skimming trench during partial fractionalization.

FIG. 1 shows a schematic diagram of a self-powered, disposable blood coagulation chip 10 that is configured to simultaneously monitor both coagulation time and hematocrit. Prothrombin time (PT) measures the clotting tendency of blood by way of the extrinsic coagulation pathway, and is the most common technique used to determine the International Normalized Ratio (INR). The dosage level of anticoagulant that is administered to a patient is determined with the INR, with lower values indicating a risk of unwanted clotting.

Additionally, blood coagulation chip 10 comprises an integrated sensor for measurement of hematocrit, which is an important indicator of homeostasis in blood. Hemorrhage is the most common side affect of anticoagulants as doctors tend to favor prescribing a higher dosage and an abnormal hematocrit level, as measured on our blood chip, would indicate the presence of internal bleeding. As many as 6% of patients taking anticoagulants report annual incidents of major hemorrhage and the additional monitoring of hematocrit would act as a valuable tool to help alert to any unknown internal bleeding.

In the embodiment shown in FIG. 1, the inventive self-powered blood chip 10 is fabricated out of a transparent, nanoporous polymer base or substrate 12. In a prototype embodiment, the polymer polydimethylsiloxane (PDMS) was used for the substrate 12. However, it is envisioned other polymers that are known in the art and particularly suitable for mass fabrication, may be employed.

The chip 10 is preferably vacuum packaged (not shown) so that the polymer 12 nanopores retain the vacuum for a period of time (e.g. up to 15 minutes or more) after the packaging is opened. Chip 10 comprises an on board lancet 14 (which may be retractably housed within substrate 12 with spring 16) that is configured to pierce the skin 28 to create a blood droplet for sampling. The blood sample may then be placed on orifice 15 that is coupled to individual dead-end channels and may be employed 22, 24, and 26 via an inlet or feeding channel 18, all of which are disposed inside the chip 10. A pressure gradient between the atmosphere and the residual vacuum inside the chip 10 drives blood flow into the inlet channel 18 and up channel 22 to measure the PT/INR, channel 26 to measure hematocrit, and channel 24 to act as a control.

Referring also to FIG. 2, PT/INR is measured by the distance (shown as furthest extent 64) in which the blood flows down the length of the control channel 24 and PT/INR, channel 26. This is based on the premise that blood with a lower INR value will travel a shorter distance.

In a preferred embodiment, the extrinsic pathway of channel 22 is infused with one or more initiator agents or reagents 60 (e.g. tissue factor (III), phosphatidylcholine, and/or phosphatidylserine) that are physio-adsorbed onto the sidewalls of the channel 22 to initiate clotting. The initiator agents 60 may be loaded via sacrificial inlet ports (not shown) that are permanently sealed after chip preparation and subsequent lyophilization enables long-term storage. The reagents 60 are reconstituted upon blood flow into the channel 22.

Since the time the user waits before blood injection after opening the vacuum sealed packaging will impact the distance the blood will travel (e.g. via a decay in the vacuum within the chip 10), a control channel 24 is used as an end point reference. This control channel 24 contains an agent or reagent 66 (e.g. lyophilized anticoagulant) that is formulated to prevent clot formation. Indicia, markings 52 are positioned adjacent both the control channel 24 and INR channel 22 to quantify the values of the visible endpoint distances (62, 64) the blood travels down the control channel 24 and INR channel 22, respectively. The two endpoint distances 62, 64 of the control channel 24 and INR channel 22 have a non-linear correlation with the actual INR value. Accordingly, a chart (e.g. a table in accompanying documents, or table 70 printed on the backside of the substrate 12 (see FIG. 5)) may enable determination of the actual INR value 76 based upon the values for the control 62 and INR 64 distances (shown in FIG. 1 as having values of 1.5 and 1.3, respectively).

Referring now to FIG. 2 and FIG. 3, hematocrit is measured via a trench 20 that utilizes gravity-based sedimentation to skim plasma from the blood 30 flowing into the inlet channel 18 of the chip 10. Hematocrit is determined by partially removing a known volume of cells from blood 30 and allowing the channel 26 to fully load. The interface 40 between transparent plasma 38 and blood 30, measured from the end of the channel 26, yields the hematocrit value.

FIG. 2 shows an image demonstrating a top view of an exemplary self-powered plasma skimming trench 20 in accordance of the present invention. Blood 30 from inlet 18 enters trench 20, where the trench 20 is configured to overflow, thus creating an observable interface 40 between blood 30 and the transparent plasma 38. FIG. 3 shows a schematic diagram of the trench 20 of FIG. 2 with the plasma 38 interface with air.

Figure 4B:
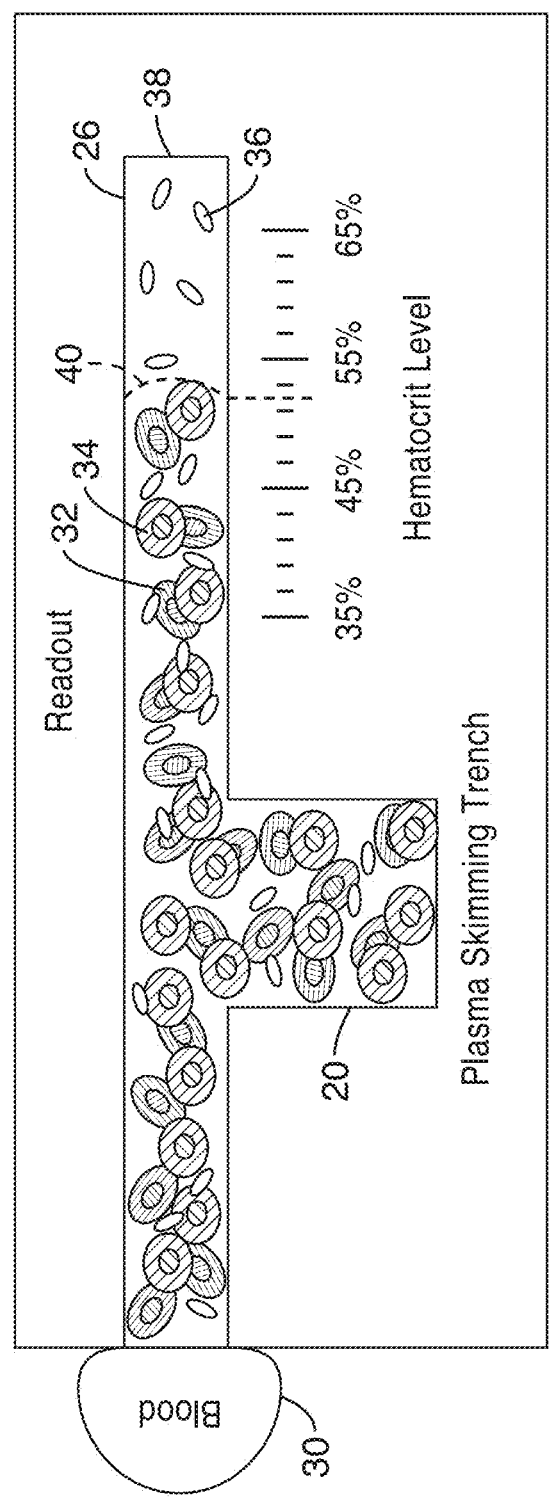
FIG. 4B is a schematic diagram of the plasma skimming trench to yield the hemocrit level.

FIG. 4A shows a schematic diagram of the interface between transparent plasma 38 and blood 30 as a result of the plasma skimming trench during partial fractionalization. White blood cells 32 and red blood cells 34 are separated from the platelets 36 in the plasma 38. FIG. 4B shows a schematic diagram of the plasma skimming trench 20 illustrating the blood 30 and plasma 38 interface 40 to yield the hemocrit level in channel 26.

The known trench 20 volume can be compared to the plasma 38 volume, as measured from the end of the dead-end channel 26. Thus, the distance in which this interface 40 travels downstream within channel 26 generally corresponds to the hematocrit level. Markers/indicia 50 printed on the substrate 12 facilitate the user making a reading of the hemocrit value.

FIG. 6 and FIG. 7 illustrate top and side view schematic diagrams of an exemplary self-loading, polymeric blood coagulation chip 80 in accordance with the present invention. Chip 80 is shown as a two-layer substrate 82, which may be both approximately 100 µm in height. The first layer 92 may comprise trenches (channels) 84, 86 and 88 for INR, control, and hemocrit measurements, respectively, that are enclosed by layer 90. Referring to the side view of FIG. 7, trench 20 for blood cell sedimentation, large vacuum reservoirs comprising inlet channel 18 and channels 84, 86 and 88, as well as inlet port 15 are shown.

The self-loading, polymeric blood coagulation chip 10/80 described above and illustrated in FIG. 1 through FIG. 7 is robust. It's porous polymeric substrate 12 can ideally withhold vacuum for years and all reagents 60, 62 are lyophilized, reconstituted by the blood introduced into the device. Different storage and packaging techniques may be used to generate the internal vacuum and maximize shelf life. The differential loading pressure between the atmosphere and the residual vacuum in the chip 10/80 may also be dependent upon atmospheric conditions and altitude. Such loading may be assessed in various conditions, and variations of the chip 10/80 may be used according to variable applications at altitude levels above (or below) sea level.

While the chip 10/80 is preferably shown above as a hybrid sensor for simultaneously measuring blood characteristics such as INR and hematocrit via an inlet channel that is bifurcated into separate channels 22, 24 and 26, it is appreciated that separate chips may be employed to individually measure specific characteristics. E.g. a first chip (not shown) may simply comprise channel 26 and trench 20 coupled to inlet channel 18 and opening 15 to measure hemocrit, and a second chip (not shown) may merely comprise control channel 24 and INR channel 22 coupled to inlet channel 18 and opening 15 to measure INR. Furthermore, the hybrid sensor chip 10/80 illustrated in FIG. 1 through FIG. 7 above may also incorporate additional channels to include measurements of other physiological characteristics of the sample blood 30.

In summary, the present invention provides a solution to the adoption of self-management for individuals who chronically rely on orally administered anticoagulants. The self-loading, polymeric blood coagulation chip 10/80 of the present invention augments self-testing through the development of a cheap, disposable tool to simultaneously measure INR and hematocrit values. We aim to decrease hospital visitation and laboratory diagnostic costs, increase patient education through self-monitoring, and aid in the adoption and practice of self-management for oral anticoagulants.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art.

From the discussion above it will be appreciated that the invention can be embodied in various ways, including the following:

1. An apparatus for measuring one or more physiological characteristics of a blood sample, the apparatus comprising: a substrate; a hematocrit measurement channel disposed within the substrate; the hematocrit measurement channel comprising a first closed end and a second end coupled to an orifice for receiving the blood sample; and a plasma skimming trench between the second end of the hematocrit measurement channel and the orifice; wherein the plasma skimming trench is configured to skim plasma from the blood sample flowing into the hematocrit measurement channel to generate a visible interface between the skimmed plasma and the blood sample; and wherein the location of the interface when the blood sample is fully loaded in said hematocrit measurement channel is indicative of the hematocrit level of the blood sample.

2. An apparatus as in any of the previous embodiments, further comprising: one or more markings on the substrate adjacent to the hematocrit measurement channel; wherein the location of the interface with respect to the one or more markings indicate a value corresponding to the hematocrit level of the blood sample.

3. An apparatus as in any of the previous embodiments: wherein the trench is configured to generate gravity-based sedimentation to skim plasma from the blood sample; and wherein the hematocrit level is a function of sedimentation of blood cells into the trench and the interface between blood cells that have overfilled the trench and the plasma.

4. An apparatus as in any of the previous embodiments, further comprising: an inlet channel in communication with the orifice and hematocrit measurement channel; wherein the substrate comprises a self-loading, porous polymeric chip configured to be sealed under vacuum to generate a vacuum within the inlet channel; and wherein a residual vacuum remains within the inlet channel such that the blood sample placed at the orifice is drawn into the hematocrit measurement channel by a pressure gradient between the atmosphere and the residual vacuum.

5. An apparatus as in any of the previous embodiments: wherein the polymeric chip is configured to be packaged in a vacuum sealed container to maintain the vacuum within the inlet channel; and wherein when the polymeric chip is configured such that when the vacuum sealed container is opened, a residual vacuum is maintained within in the inlet channel and hematocrit measurement channel.

6. An apparatus as in any of the previous embodiments, further comprising: a prothrombin time (PT) measurement channel disposed within the substrate; the PT measurement channel comprising a first closed end and a second end coupled to the inlet channel; wherein the residual vacuum is configured to draw the blood sample into the PT measurement channel to measure PT (INR value) associated with the blood sample.

7. An apparatus as in any of the previous embodiments, wherein the self-loading, porous polymeric chip is configured to simultaneously measure hematocrit and PT (INR value).

8. An apparatus as in any of the previous embodiments, wherein the PT measurement channel comprises one or more coagulant reagents configured to initiate clotting of the blood sample.

9. An apparatus as in any of the previous embodiments, wherein INR value is determined by the distance the blood sample traverses down the PT measurement channel before it coagulates.

10. An apparatus as in any of the previous embodiments, wherein the one or more coagulant reagents comprise one or more of the following agents that are physio-adsorbed into the PT channel: tissue factor (III), phosphatidylcholine, and phosphatidylserine.

11. An apparatus as in any of the previous embodiments, further comprising: a control measurement channel coupled to the inlet channel; wherein the residual vacuum is configured to draw the blood sample into the control measurement channel to provide an end-point reference.

12. An apparatus as in any of the previous embodiments, wherein the control channel comprises an anticoagulant reagent configured to prevent clotting of the blood sample.

13. An apparatus as in any of the previous embodiments: wherein the one or more coagulant reagents and anticoagulant reagent are lyophilized prior to packaging; and wherein the reagents are reconstituted upon contact with the blood sample.

14. An apparatus for measuring one or more physiological characteristics of a blood sample, the apparatus comprising: a substrate; a prothrombin time (PT) measurement channel disposed within the substrate; the PT measurement channel being configured to measure PT (INR value) associated with the blood sample; the PT measurement channel comprising a first closed end and a second end coupled to an orifice for receiving the blood sample; and wherein INR value is determined by the distance the blood sample traverses down the PT measurement channel before it coagulates.

15. An apparatus as in any of the previous embodiments, further comprising: one or more markings on the substrate adjacent to the PT measurement channel; the one or more markings indicative of the INR value.

16. An apparatus as in any of the previous embodiments, further comprising: an inlet channel in communication with the orifice and PT measurement channel; wherein the substrate comprises a self-loading, porous polymeric chip configured to be sealed under vacuum to generate a vacuum within the inlet channel; and wherein a residual vacuum remains within the inlet channel such that the blood sample placed at the orifice is drawn into the PT measurement channel by a pressure gradient between the atmosphere and the residual vacuum.

17. An apparatus as in any of the previous embodiments: wherein the polymeric chip is configured to be packaged in a vacuum sealed container to maintain the vacuum within the inlet channel; and wherein when the polymeric chip is configured such that when the vacuum sealed container is opened, a residual vacuum is maintained within the inlet channel and PT measurement channel.

18. An apparatus as in any of the previous embodiments, wherein the PT measurement channel comprises one or more coagulant reagents configured to initiate clotting of the blood sample.

19. An apparatus as in any of the previous embodiments, wherein the INR value is determined by the distance the blood sample traverses down the PT measurement channel before it coagulates.

20. An apparatus as in any of the previous embodiments, wherein the one or more coagulant reagents comprise one or more of the following agents that are physio-adsorbed into the PT channel: tissue factor (III), phosphatidylcholine, and phosphatidylserine.

21. An apparatus as in any of the previous embodiments, further comprising: a control measurement channel coupled to the inlet channel; wherein the residual vacuum is configured to draw the blood sample into the control measurement channel to provide an end-point reference.

22. An apparatus as in any of the previous embodiments, wherein the control channel comprises an anticoagulant reagent configured to prevent clotting of the blood sample.

23. An apparatus as in any of the previous embodiments: wherein the one or more coagulant reagents and anticoagulant reagent are lyophilized prior to packaging; and wherein the reagents are reconstituted upon contact with the blood sample.

24. An apparatus as in any of the previous embodiments, further comprising: a hematocrit measurement channel disposed within the substrate; the hematocrit measurement channel comprising: a first closed end; and a second end coupled to the inlet channel; and a plasma skimming trench between the second end of the hematocrit measurement channel and the inlet; wherein the plasma skimming trench is configured to skim plasma from the blood sample flowing into the channel to generate a visible interface between the skimmed plasma and the blood sample; and wherein the location of the interface when the blood sample is fully loaded in said hematocrit measurement channel is indicative of the hematocrit level of the blood sample.

25. An apparatus as in any of the previous embodiments: wherein the trench is configured to generate gravity-based sedimentation to skim plasma from the blood sample; and wherein the hematocrit level is a function of sedimentation of blood cells into the trench and the interface between blood cells that have overfilled the trench and the plasma.

26. An apparatus as in any of the previous embodiments, wherein the self-loading, porous polymeric chip is configured to simultaneously measure hematocrit and PT (INR value).

27. A method for measuring one or more physiological characteristics of a blood sample, the method comprising: providing a substrate having one or more measurement channels embedded within the substrate; establishing a vacuum within the one or more measurement channels; applying a blood sample to an orifice of the substrate; said orifice coupled to the one or more measurement channels; drawing the blood sample into the one or more measurement channels as a result of the pressure gradient between the atmosphere and a residual vacuum within the one or more measurement channels; and measuring a physiological characteristic associated with the blood sample as a function of the distance the blood sample travels within the one or more measurement channels.

28. A method as in any of the previous embodiments: wherein the physiological characteristic comprises hematocrit; the one or more measurement channels comprising a hematocrit measurement channel disposed within the substrate; the hematocrit measurement channel comprising a first closed end and a second end coupled to the orifice for receiving the blood sample; skimming plasma from the blood sample flowing into the hematocrit measurement channel to generate a visible interface between the skimmed plasma and the blood sample; and locating of the interface when the blood sample is fully loaded in said hematocrit measurement channel to indicate the hematocrit level of the blood sample.

29. A method as in any of the previous embodiments: wherein the hematocrit measurement channel comprises a plasma skimming trench between the second end of the hematocrit measurement channel and the orifice; wherein skimming plasma from the blood sample comprises generating gravity-based sedimentation to skim plasma from the blood sample; and wherein the hematocrit level is a function of sedimentation of blood cells into the trench and the interface between blood cells that have overfilled the trench and the plasma.

30. A method as in any of the previous embodiments: wherein the substrate further comprises a polymeric chip with an inlet channel in communication with the orifice and hematocrit measurement channel; and wherein establishing a vacuum comprises sealing the polymeric chip under vacuum to generate a vacuum within the inlet channel.

31. A method as in any of the previous embodiments: wherein sealing the polymeric chip comprises packaging the chip in a vacuum sealed container to maintain the vacuum within the inlet channel; and wherein when the polymeric chip is configured such that when the vacuum sealed container is opened a residual vacuum is maintained within in the inlet channel and hematocrit measurement channel.

32. A method as in any of the previous embodiments, further comprising: measuring a prothrombin time (PT) via measurement channel disposed within the substrate; the PT measurement channel comprising a first closed end and a second end coupled to the inlet channel; wherein the residual vacuum is configured to draw the blood sample into the PT measurement channel to measure PT (INR value) associated with the blood sample.

33. A method as in any of the previous embodiments, wherein the hematocrit and PT (INR value) are measured simultaneously.

34. A method as in any of the previous embodiments, wherein the PT measurement channel comprises one or more coagulant reagents configured to initiate clotting of the blood sample.

35. A method as in any of the previous embodiments, wherein INR value is determined by the distance the blood sample traverses down the PT measurement channel before it coagulates.

36. A method as in any of the previous embodiments, wherein the one or more coagulant reagents comprise one or more of the following agents that are physio-adsorbed into the PT channel: tissue factor (III), phosphatidylcholine, and phosphatidylserine.

37. A method as in any of the previous embodiments, further comprising: measuring a control value via a control measurement channel coupled to the inlet channel; wherein the residual vacuum is configured to draw the blood sample into the control measurement channel to provide an end-point reference.

38. A method as in any of the previous embodiments, wherein the control channel comprises an anticoagulant reagent configured to prevent clotting of the blood sample.

39. A method as in any of the previous embodiments, further comprising: lyophilizing the one or more coagulant reagents and anticoagulant reagent prior to packaging; and reconstituting the reagents upon contact with the blood sample.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for measuring one or more physiological characteristics of a blood sample, the apparatus comprising:
a substrate;
a hematocrit measurement channel disposed within the substrate;
the hematocrit measurement channel comprising a first closed end and a second end coupled to an orifice for receiving the blood sample; and
a plasma skimming trench between the second end of the hematocrit measurement channel and the orifice;
wherein the plasma skimming trench is configured to skim plasma from the blood sample flowing into the hematocrit measurement channel to generate a visible interface between the skimmed plasma and the blood sample;
wherein the location of the interface when the blood sample is fully loaded in said hematocrit measurement channel is indicative of the hematocrit level of the blood sample; and
an inlet channel in communication with the orifice and hematocrit measurement channel;
wherein the substrate comprises a self-loading, porous polymeric chip configured to be sealed under vacuum to generate a vacuum within the inlet channel; and
wherein a residual vacuum remains within the inlet channel such that the blood sample placed at the orifice is drawn into the hematocrit measurement channel by a pressure gradient between the atmosphere and the residual vacuum.

2. An apparatus as recited in claim 1, further comprising:
one or more markings on the substrate adjacent to the hematocrit measurement channel;
wherein the location of the interface with respect to the one or more markings indicate a value corresponding to the hematocrit level of the blood sample.

3. An apparatus as recited in claim 1:
wherein the trench is configured to generate gravity-based sedimentation to skim plasma from the blood sample; and
wherein the hematocrit level is a function of sedimentation of blood cells into the trench and the interface between blood cells that have overfilled the trench and the plasma.

4. An apparatus as recited in claim 1:
Wherein the polymeric chip is configured to be packaged in a vacuum sealed container to maintain the vacuum within the inlet channel; and
Wherein when the polymeric chip is configured such that when the vacuum sealed container is opened, a residual vacuum is maintained within the inlet channel and hematocrit measurement channel.

5. An apparatus as recited in claim 1, further comprising:
a prothrombin time (PT) measurement channel disposed within the substrate;
the PT measurement channel comprising a first closed end and a second end coupled to the inlet channel;
wherein the residual vacuum is configured to draw the blood sample into the PT measurement channel to measure PT (INR value) associated with the blood sample.

6. An apparatus as recited in claim 5, wherein the self-loading, porous polymeric chip is configured to simultaneously measure hematocrit and PT (INR value).

7. An apparatus as recited in claim 5, wherein the PT measurement channel comprises one or more coagulant reagents configured to initiate clotting of the blood sample.

8. An apparatus as recited in claim 7, wherein INR value is determined by the distance the blood sample traverses down the PT measurement channel before it coagulates.

9. An apparatus as recited in claim 8, further comprising:
a control measurement channel coupled to the inlet channel;
wherein the residual vacuum is configured to draw the blood sample into the control measurement channel to provide an end-point reference.

10. An apparatus as recited in claim 9, wherein the control channel comprises an anticoagulant reagent configured to prevent clotting of the blood sample.

11. An apparatus as recited in claim 10:
wherein the one or more coagulant reagents and anticoagulant reagent are lyophilized prior to packaging; and
wherein the reagents are reconstituted upon contact with the blood sample.

12. An apparatus as recited in claim 7, wherein the one or more coagulant reagents comprise one or more of the following agents that are physio-adsorbed into the PT channel: tissue factor (III), phosphatidylcholine, and phosphatidylserine.

13. An apparatus for measuring one or more physiological characteristics of a blood sample, the apparatus comprising:
a substrate;
a prothrombin time (PT) measurement channel disposed within the substrate;
the PT measurement channel being configured to measure PT (INR value) associated with the blood sample;
the PT measurement channel comprising a first closed end and a second end coupled to an orifice for receiving the blood sample;
wherein INR value is determined by the distance the blood sample traverses down the PT measurement channel before it coagulates; and
an inlet channel in communication with the orifice and PT measurement channel;
wherein the substrate comprises a self-loading, porous polymeric chip configured to be sealed under vacuum to generate a vacuum within the inlet channel; and
wherein a residual vacuum remains within the inlet channel such that the blood sample placed at the orifice is drawn into the PT measurement channel by a pressure gradient between the atmosphere and the residual vacuum.

14. An apparatus as recited in claim 13, further comprising:
one or more markings on the substrate adjacent to the PT measurement channel;
the one or more markings indicative of the INR value.

15. An apparatus as recited in claim 13:
wherein the polymeric chip is configured to be packaged in a vacuum sealed container to maintain the vacuum within the inlet channel; and
wherein when the polymeric chip is configured such that when the vacuum sealed container is opened, a residual vacuum is maintained within the inlet channel and PT measurement channel.

16. An apparatus as recited in claim 13, wherein the PT measurement channel comprises one or more coagulant reagents configured to initiate clotting of the blood sample.

17. An apparatus as recited in claim 16, wherein the INR value is determined by the distance the blood sample traverses down the PT measurement channel before it coagulates.

18. An apparatus as recited in claim 17, further comprising:
a control measurement channel coupled to the inlet channel;
wherein the residual vacuum is configured to draw the blood sample into the control measurement channel to provide an end-point reference.

19. An apparatus as recited in claim 18, wherein the control channel comprises an anticoagulant reagent configured to prevent clotting of the blood sample.

20. An apparatus as recited in claim 19:
wherein the one or more coagulant reagents and anticoagulant reagent are lyophilized prior to packaging; and
wherein the reagents are reconstituted upon contact with the blood sample.

21. An apparatus as recited in claim 16, wherein the one or more coagulant reagents comprise one or more of the following agents that are physio-adsorbed into the PT channel: tissue factor (III), phosphatidylcholine, and phosphatidylserine.

22. An apparatus as recited in claim 13, further comprising:
a hematocrit measurement channel disposed within the substrate;
the hematocrit measurement channel comprising:
a first closed end; and
a second end coupled to the inlet channel; and
a plasma skimming trench between the second end of the hematocrit measurement channel and the inlet;
wherein the plasma skimming trench is configured to skim plasma from the blood sample flowing into the channel to generate a visible interface between the skimmed plasma and the blood sample; and
wherein the location of the interface when the blood sample is fully loaded in said hematocrit measurement channel is indicative of the hematocrit level of the blood sample.

23. An apparatus as recited in claim 22:
wherein the trench is configured to generate gravity-based sedimentation to skim plasma from the blood sample; and wherein the hematocrit level is a function of sedimentation of blood cells into the trench and the interface between blood cells that have overfilled the trench and the plasma.

24. An apparatus as recited in claim 22, wherein the self-loading, porous polymeric chip is configured to simultaneously measure hematocrit and PT (INR value).

\* \* \* \* \*